United States Patent [19]

Rodson et al.

[11] Patent Number: 6,113,935
[45] Date of Patent: Sep. 5, 2000

[54] WATER-IN-OIL MICROENCAPSULATION PROCESS AND MICROCAPSULES PRODUCED THEREBY

[75] Inventors: Maurius Rodson, El Sobrante; Herbert B. Scher, Moraga, both of Calif.

[73] Assignee: ZENECA Limited, United Kingdom

[21] Appl. No.: 08/994,316

[22] Filed: Dec. 19, 1997

Related U.S. Application Data

[60] Provisional application No. 60/093,059, Dec. 31, 1996.

[51] Int. Cl.$^7$ .............................. A01N 25/34; A61K 9/52; A61K 9/16; B01J 13/02
[52] U.S. Cl. ......................... 424/408; 424/457; 424/497; 264/4.7
[58] Field of Search .............................. 264/4.7; 424/408, 424/457, 497

[56] References Cited

U.S. PATENT DOCUMENTS

| | | | |
|---|---|---|---|
| 3,669,899 | 6/1972 | Vassiliades et al. | 252/316 |
| 4,157,983 | 6/1979 | Golden | 252/316 |
| 4,534,783 | 8/1985 | Beestman | 71/27 |
| 4,956,129 | 9/1990 | Scher et al. | 264/4.7 |
| 4,977,059 | 12/1990 | Liang et al. | 530/138 |
| 5,225,278 | 7/1993 | Kielbania, Jr. et al. | 428/402.22 |
| 5,268,130 | 12/1993 | Seitz | 264/4.7 |
| 5,326,757 | 7/1994 | Demopoulos | 514/167 |
| 5,332,584 | 7/1994 | Scher et al. | 424/408 |
| 5,401,577 | 3/1995 | Seitz | 428/402.21 |
| 5,666,785 | 9/1997 | Jouffreau et al. | 53/411 |
| 5,858,384 | 1/1999 | Levy | 424/406 |

*Primary Examiner*—Thurman K. Page
*Assistant Examiner*—Todd D Ware
*Attorney, Agent, or Firm*—David P. LeCroy

[57] ABSTRACT

A suspension of microcapsules in an organic liquid, the microcapsules containing an aqueous phase, is produced by interfacial polymerization in the presence of a proton transfer catalyst of a water-in-oil emulsion in which the aqueous phase contains a urea/formaldehyde or melamine/formaldehyde prepolymer.

29 Claims, No Drawings

WATER-IN-OIL MICROENCAPSULATION PROCESS AND MICROCAPSULES PRODUCED THEREBY

This application claims the benefit of Provisional Application No. 60/093,059, filed Dec. 31, 1996.

BACKGROUND AND PRIOR ART

This invention relates to a novel process for producing microencapsulated materials by a water-in-oil microencapsulation process, whereby microcapsules are formed which contain aqueous materials.

Numerous processes are known in the art for producing microencapsulated materials. Nearly all the known processes produce microcapsules of materials contained in a water-immiscible or insoluble material and are produced by what is termed oil-in-water microencapsulation processes. These in general involve the production of a dispersion of "oil" or organic, substantially water-immiscible liquid droplets (discontinuous phase) in an aqueous medium (continuous phase). The oil droplets contain one or more monomers or prepolymers and microcapsules are formed by subjecting the emulsion to conditions such as temperature and/or pH and/or agitation to cause polymerization of the monomers or prepolymers present in the oil phase to produce microcapsules having a polymeric shell enclosing the water-immiscible droplet phase. Such processes are described, for example, in U.S. Pat. Nos. 4,285,720 and 4,956,129. The former involves production of microcapsules of a polyurea material and the latter of an etherified urea-formaldehyde polymer.

On the other hand, there is comparatively little information available on the production of microcapsules containing an aqueous material by a water-in-oil microencapsulation process. One process which somewhat approaches a water-in-oil microencapsulation process is described in U.S. Pat. No. 4,157,983. In that process, a mixture is formed which contains an emulsifier, a water-immiscible liquid, a urea-formaldehyde prepolymer, a water-dispersible material to be encapsulated, and water. The mixture is agitated to produce a water-in-oil emulsion. The emulsion is then cured or treated to produce microcapsules by solidification of the urea-formaldehyde prepolymer resin to form a matrix encapsulating the droplets and permitting the separation of solid polymeric capsules containing the water-dispersible material. The curing or polymerization is instituted by use of an amphiphatic catalyst, that is, a catalyst which is soluble in both the water and oil phases of the emulsion. However, the products of this process are not true microcapsules but rather comprise a matrix of the urea/formaldehyde polymer containing the water dispersible material.

U.S. Pat. No. 4,534,783 discloses a process for encapsulating aqueous materials using two monomers or prepolymers.

It is an object of the present invention to provide a simple method for producing true microcapsules containing an aqueous liquid core, of relatively uniform and controlled size, which are suitable for use without further treatment.

SUMMARY OF THE INVENTION

This invention comprises a process for the production of microcapsules containing an aqueous material within a polymeric shell, said process comprising (a) providing an aqueous phase comprising a material to be encapsulated, and a urea-formaldehyde and/or melamine-formaldehyde prepolymer dissolved therein; (b) creating an emulsion of said aqueous phase in a continuous organic liquid phase comprising one or more organic solvents and one or more surface active agents, wherein the emulsion comprises discrete droplets of the aqueous phase dispersed in the continuous organic liquid phase, there being formed thereby an interface between the discrete droplets of the aqueous phase and the continuous organic liquid phase; and (c) causing in situ self-condensation of the prepolymer in the aqueous phase of the discrete droplets adjacent to the interface by heating the emulsion to a temperature of from about 20 to about 100° C. in the presence of a surface active proton transfer catalyst which is soluble in the organic liquid but only slightly soluble in the aqueous phase for a sufficient period of time to allow substantial completion of in situ condensation of the prepolymer to convert the liquid droplets of the aqueous medium to capsules consisting of solid polymer shells enclosing the aqueous medium.

This invention also pertains to microcapsules produced by the above process.

DETAILED DESCRIPTION OF THE INVENTION

The process of this invention is useful for producing microcapsules containing aqueous media having various ingredients dissolved and/or suspended therein, or even microcapsules containing only water, should there be a need for production of such capsules. The following is a description of both the essential and optional features of this process and the products produced therefrom:

Aqueous Medium

The aqueous medium to be encapsulated may consist only of water, but preferably is an aqueous medium which contains one or more ingredients to be microencapsulated dissolved, dispersed and/or suspended in the water.

This process is applicable to production of microcapsules containing one or more ingredients dissolved, dispersed and/or suspended in the aqueous medium. A wide variety of ingredients can be encapsulated by the present process providing such materials do not react either with each other or with the prepolymer, or with any other components utilized in the overall encapsulation system.

The encapsulated material can be selected from various water-soluble substances suitable for encapsulation such as water-soluble pesticides and other bioactive materials, colors, dyes, inks and the like. For convenience, this invention is described and exemplified in terms of pesticides.

This process is particularly suitable for production of microencapsulated pesticides such as herbicides, insecticides, fungicides, nematicides, bactericides, rodenticides, bactericides and the like, and non-pesticidal materials used for pest control or otherwise in related activities such as agriculture and domestic, commercial or industrial pest control such as biocides, animal, insect or bird repellents, plant or insect or insect growth regulators, pheromones, fertilizers, sex attractants, and flavor and odor compositions.

Some examples of water soluble materials which may be encapsulated by this process include the pesticides paraquat, diquat, glyphosate, dicamba, ioxynil, bromoxynil, bentazon, acifluorfen, and fomesafen, all in either acid or salt forms. Also suitable for inclusion in the capsules of this invention are water-dispersible high melting point pesticides such as atrazine and azoxystrobin.

Also contained in the aqueous medium is a urea-formaldehyde and/or melamine-formaldehyde prepolymer. These prepolymers have a high solubility in water and a relatively low solubility in the organic liquid to be utilized in this process. The prepolymer contains a large number of methylol (CH$_2$OH) groups in its molecular structure. These prepolymers are commercially available generally as aqueous solutions or as water-soluble solids for use as adhesives and include products such as Cymel 401 and 481, available from Cytec Industries and Resin CR-583, available from Borden Chemicals Inc. The prepolymers can also be prepared by known techniques such as the base catalyzed reaction between urea and formaldehyde or between melamine and formaldehyde at a weight ratio of 0.6 to 1.3 parts formaldehyde to one part urea or melamine.

The concentration of the prepolymer in the aqueous phase is not critical to the practice of the invention but can vary over a wide range, depending on the desired capsule wall strength and the desired quantity of aqueous liquid in the finished capsule. Most conveniently, however, the prepolymer concentration in the aqueous phase is from about 1% to about 70% on a weight basis, preferably from about 5% to about 50%.

In addition to, or instead of, a dissolved active ingredient, the aqueous phase may contain one or more high melting solid active ingredients which are suspended or dispersed in the medium. With respect to pesticides, such materials may be for instance atrazine or azoxystrobin. Such compositions may also contain one or more dispersants.

In addition to the active ingredient included in the aqueous phase, an active ingredient may also be included in the organic phase, though it will not be included in any microcapsules formed. However, inclusion of a second active ingredient, for example, a second pesticide, in the organic phase allows the production of organic suspensions of microcapsules containing two pesticides to be used in combination. For instance, an oil soluble herbicide such as diuron may be included in the organic phase to be used in combination with paraquat or diquat in the microencapsulated aqueous phase. Alternatively, an oil-soluble insecticide may be included in the organic phase so as to produce an overall microcapsule suspension containing both a herbicide and an insecticide, the former encapsulated, the latter not.

Oil-soluble (and correspondingly water-insoluble) pesticides which may be included in the nonencapsulated organic phase of a capsule suspension include thiocarbamate herbicides such as EPTC, butylate, cycloate, molinate, or vernolate; haloacetanilide herbicides such as acetochlor, metolachlor, alachlor, butachlor and propachlor; nitroaniline herbicides such as trifluralin, organophosphorus insecticides such as parathion, malathion, and fonofos; pyrethroid insecticides such as permethrin, lambda-cyhalothrin, deltamethrin, tralomethrin, cypermethrin, and tefluthrin; and fungicides such as azoxystrobin.

Additionally, the overall formulation may contain synergists, activators, safeners and the like for the active pesticides.

Emulsion Formation

Once the aqueous phase has been prepared, an emulsion is formed by dispersing it in an organic or water-immiscible liquid.

The organic liquid generally contains one or more solvents, one or more surfactants or surface-active agents, and a proton transfer catalyst as described below. The solvents utilized in this process are organic solvents, preferably hydrocarbons or mixtures of hydrocarbons such as Solvent 450 (a kerosene fraction, available from VWR Inc.), Union 76 18-90 oil (a paraffinic solvent available from Union Oil Company); Diesel oil #2; Aromatic 100 and 200 solvents, available from Exxon; and Suresol 100 and 190 solvents, available from Koch Refinery Co.

The surfactant or surface active agent can be any of the many such materials known to be useful for lowering the surface tension of a fluid interface, and can be either a nonionic or anionic type. Examples of nonionic surfactants are long chain alkyl and mercaptan polyethoxy alcohols, alkylaryl polyoxyethylene alcohols (such as ethoxylated nonylphenols), alkylaryl polyether alcohols, alkyl polyether alcohols, polyoxyethylene sorbitan fatty acid esters, polyoxyethylene ethers, and esters of polyalkylene glycols (particularly polyethylene glycol) with fatty or rosin acids. Preferred anionic surfactants are the calcium, amine, alkanolamine and alkali metal salts of alkyl and alkylaryl sulfonates, vegetable oil sulfonates and ethoxylated or propoxylated mono- and diethers of phosphoric acid. Blends of surfactants are also useful. Preferred surfactants used in this process are the ethoxylated nonylphenols.

The amount of surface active agent is not critical to the invention and can vary widely. For convenience, the surface active agent generally comprises from about 0.1% to about 5.0% by weight of the organic phase. It may be added either before or after the emulsion is formed.

The organic liquid also contains an effective amount of a proton transfer catalyst which catalyzes the formation of the polymeric wall. The proton transfer catalyst may be added before or at the emulsion forming stage or subsequently, prior to polymerization and wall formation. However, it is preferably added prior to the formation of the emulsion because it possesses surface active properties which are useful in the emulsion formation step. When the proton transfer catalyst is present prior to emulsion formation, it is advisable to maintain the temperature of the mixture at a maximum of about room temperature to avoid or minimize premature formation of the polymer.

The proton transfer catalyst is an acidic material which is essentially oil soluble and at most very slightly soluble in water. However, the molecular structure of the proton transfer catalyst includes a large hydrophobic portion and an ionic moiety which is capable of transferring across the oil/water interface into the water side, carrying with it a catalytic proton which causes polymerization of the prepolymer in the aqueous medium to form the shell wall of the microcapsule at the oil/water phase interface. The hydrophobic portion of the molecule remains anchored in the oil phase in a stationary way while the proton carrying moiety remains anchored on the water side of the interface. This produces an immobilized catalytic layer which limits the polymerization of the resin to the interface region, forming a relatively thin shell wall around the aqueous droplets. This is in contrast to the amphiphatic catalyst described in U.S. Pat. No. 4,157,983, which is soluble in the aqueous phase and thus causes polymerization of the resin throughout the phase, forming a matrix rather than a microcapsule.

Preferably the proton transfer catalyst is a sulfonic acid having at least 20 carbon atoms in the molecule. The sulfonic acid may be saturated or unsaturated, cyclic or acyclic; e.g., it may be an alkyl, alkenyl, alkynyl, aryl, alkaryl, or other type of sulfonic acid. The molecule may include other substituents, such as halogen atoms, so long as it contains 20 or more carbon atoms, is essentially oil soluble and at most only slightly soluble in water. Most preferably, the proton transfer catalyst is a long chain alkylaryl sulfonic acid such as an alkylbenzene or alkylnaphthalene sulfonic acid in which the alkyl group contains from about 16 to about 24 carbon atoms. A preferred proton transfer catalyst is didodecylbenzene sulfonic acid.

The droplet size in the emulsion is not critical to the invention. For greatest utility of the final product, the droplet size will fall in the range of about 0.5 microns to about 4000 microns in diameter. The preferred range for most pesticidal applications is from about 1 micron to about 100 microns in diameter. The emulsion is prepared by the use of any conventional high shear stirring device. Once the desired droplet size is attained, mild agitation is sufficient to prevent segregation of the sample throughout the balance of the process.

As the polymer wall becomes more rigid, contact between the active groups on the prepolymer becomes increasingly more difficult. Thus, the in situ self-condensation polymerization reaction is self-terminating and is generally allowed to run to completion.

The rate of the in situ self-condensation polymerization reaction increases with both acidity and temperature. The reaction can therefore be conducted anywhere within the range of about 20° C. to about 100° C., preferably between about 40° C. and about 70° C. At the low end of this range, polymer formation is sufficiently slow so as not to cause premature formation of the shell wall. Therefore, the temperature is preferably maintained at about 20–25° C. until the desired droplet size has been reached, then increased to hasten formation of the polymer shell wall around the droplets. The reaction will generally be complete within a few hours, although with high acidity and high temperature, the reaction can be completed within minutes.

Once the capsules are formed, they can be stored and used as a dispersion, or filtered and recovered as dried capsules. In either form, the capsules are useful and effective in the controlled release of the core liquid. Dispersions are preferably stabilized by thickeners dissolved in the continuous phase. Any conventional thickener can be used. Typical thickeners include hydrogenated castor oil, organically treated clays, and organically treated silica.

One feature of this invention is that the capsules or capsule suspensions hereof may be packaged in water-soluble packaging materials, for instance, packets or bags formed from water-soluble polymers such as polyvinyl alcohol and the like. Thus, the process of this invention provides, in essence, a means of delivering a water-soluble pesticide in a water-soluble package.

The following examples are illustrative of both the processes and product of the present invention but are not intended to define or limit it in any manner.

EXAMPLE 1

An organic phase was prepared by dissolving 12.0 grams dodecylbenzene sulfonic acid (Aristol A, available from Pilot Chemical Co.) and 12.0 grams of a nonionic alkylaryl phenol surfactant (Igepal CA-630, available from Rhone-Poulenc) in 169.0 g kerosene solvent (Solvent 450, available from VWR Co.). The aqueous phase was prepared by dissolving 100.0 g technical grade paraquat and 50.0 g urea/formaldehyde prepolymer (Casco SR-397C resin, available from Borden Chemical) in 50.0 g water. The two phases were then combined with thorough stirring to produce the water-in-oil emulsion. Then, the temperature was raised to 40° C. and stirring continued for two more hours. The resulting product was cooled to produce a suspension of microcapsules in the organic phase (primarily the solvent), the microcapsules enclosing the aqueous medium.

Similarly, other microencapsulated formulations of paraquat were prepared as described in the following Table 1. The materials utilized in the examples in Table 1 were, in addition to those mentioned above, WS-351-38c prepolymer (urea/formaldehyde, available from Borden), Aristol E proton transfer catalyst (didodecylbenzenesulfonic acid, available from Pilot Chemical Co.), and as surfactants Neodol 25-3 (linear primary alcohol ethoxylate, available from Shell Chemicals) and Tergitol NP9 and NP13 (ethoxylated nonylphenols, available from Union Carbide).

There was no recombination of capsules in all the examples below except for examples 4 and 8. The particle size varied from approximately 30 microns or less up to approximately 300 microns or less, depending on the example, and no coalescence was observed in any run except example 7.

TABLE 1

| INGREDIENTS, G. | EXAMPLE | | | | | | |
|---|---|---|---|---|---|---|---|
| | 2 | 3 | 4 | 5 | 6 | 7 | 8 |
| Aqueous Phase | | | | | | | |
| Paraquat, technical grade | 100.0 | 150.0 | 150.0 | 150.0 | 150.0 | 150.0 | 150.0 |
| WS-351-380 prepolymer water | 50.0 | 50.0 | 50.0 | 50.0 | 50.0 | 50.0 | 50.0 |
| Organic Phase | | | | | | | |
| Union 76 IV-90 solvent | 173 | 169.0 | — | 169.0 | 169.0 | 169.0 | 169.0 |
| Solvent 450 | — | — | 169.0 | — | — | — | — |
| Aristol A catalyst | 12.0 | 12.0 | 12.0 | 12.0 | — | — | — |
| Aristol E catalyst | — | — | — | — | 12.0 | — | 12.0 |
| Aristol 360 catalyst | — | — | — | — | — | 12.0 | — |
| Neodol 25-3 surfactant | 8.0 | — | — | — | — | — | — |
| Igepal CA-630 surfactant | — | 12.0 | 8.0 | — | — | — | — |
| Tergigol NP 13 surfactant | — | — | — | 12.0 | 12.0 | 12.0 | — |
| Tergitol NP 9 surfactant | — | — | — | — | — | — | 12.0 |

What is claimed is:

1. A process for the production of microcapsules containing an aqueous material within a polymeric shell, said process comprising:
   (a) providing an aqueous phase comprising a material to be encapsulated, and a urea-formaldehyde and/or melamine-formaldehyde prepolymer dissolved therein;
   (b) creating an emulsion of said aqueous phase in a continuous organic liquid phase comprising one or more organic solvents and one or more surface active agents, wherein the emulsion comprises discrete droplets of the aqueous phase dispersed in the continuous phase organic liquid, there being formed thereby an interface between the discrete droplets of the aqueous phase and the continuous organic liquid phase; and
   (c) causing in situ self-condensation of the prepolymer in the aqueous phase of the discrete droplets adjacent to the interface by heating the emulsion to a temperature of from about 20 to about 100° C. in the presence of a surface active proton transfer catalyst which is soluble in the organic liquid but only slightly soluble in the aqueous phase for a sufficient period of time to allow substantial completion of in situ condensation of the prepolymer to convert the liquid droplets of the aqueous phase to microcapsules consisting of solid permeable polymer enclosing the aqueous material.

2. A process according to claim 1 in which the aqueous material contains an active ingredient dissolved and/or dispersed therein.

3. A process according to claim 1 in which the aqueous material contains an active ingredient dissolved therein.

4. A process according to claim 1 in which the aqueous material contains an active ingredient dispersed therein.

5. A process according to claim 3 in which the active ingredient is a bioactive material.

6. A process according to claim 5 in which the bioactive material is a pesticide.

7. A process according to claim 6 in which the bioactive material is a herbicide.

8. A process according to claim 7 in which the herbicide is paraquat.

9. A process according to claim 1 in which the organic liquid contains an active ingredient.

10. A process according to claim 9 in which the active ingredient is dissolved in the organic liquid.

11. A process according to claim 9 in which the active ingredient is dispersed in the organic liquid.

12. Microcapsules produced according to the process of claim 1.

13. A suspension of microcapsules in an organic liquid produced according to the process of claim 1.

14. Microcapsules comprising a polymeric shell wall formed of urea-formaldehyde and/or melamine-formaldehyde polymer containing an aqueous material.

15. Microcapsules according to claim 14 wherein the aqueous material comprises a water-soluble or water-dispersible bioactive material.

16. Microcapsules according to claim 15 wherein the bioactive material is a pesticide.

17. Microcapsules according to claim 15 wherein the bioactive material is a herbicide.

18. Microcapsules according to claim 17 wherein the herbicide is paraquat.

19. Microcapsules according to claim 14 wherein the microcapsules are suspended in an organic liquid.

20. A suspension of microcapsules comprising an organic liquid with microcapsules suspended therein, and wherein the microcapsules are further comprised of a polymeric shell wall formed of urea-formaldehyde and/or melamine-formaldehyde polymer containing a water-soluble or water-dispersible bioactive material.

21. A microcapsule suspension according to claim 20 wherein the microcapsules contain a water-soluble or water-dispersible pesticide.

22. A microcapsule suspension according to claim 21 wherein the pesticide is a herbicide.

23. A microcapsule suspension according to claim 20 wherein the organic liquid contains a substantially water-insoluble pesticide.

24. A microcapsule suspension according to claim 23 wherein the substantially water-insoluble pesticide is a herbicide.

25. A microcapsule suspension according to claim 23 wherein the substantially water-insoluble pesticide is an insecticide.

26. A microcapsule suspension according to claim 23 wherein the substantially water-insoluble pesticide is a fungicide.

27. A packaged pesticidal formulation comprising microcapsules according to claim 14 contained within a water-soluble packaging material.

28. A packaged pesticidal formulation comprising a microcapsule suspension according to claim 21 contained within a water-soluble packaging material.

29. A packaged pesticidal formulation comprising a microcapsule suspension according to claim 23 contained within a water-soluble packaging material.

* * * * *